United States Patent
Kimura et al.

(10) Patent No.: US 10,338,019 B2
(45) Date of Patent: Jul. 2, 2019

(54) SENSOR SUBSTRATE AND SENSOR DEVICE

(71) Applicant: KYOCERA Corporation, Kyoto-shi, Kyoto (JP)

(72) Inventors: Takashi Kimura, Kyoto (JP); Hidekazu Otomaru, Kyoto (JP)

(73) Assignee: KYOCERA CORPORATION, Kyoto (JP)

( * ) Notice: Subject to any disclaimer, the term of this patent is extended or adjusted under 35 U.S.C. 154(b) by 0 days.

(21) Appl. No.: 15/554,108

(22) PCT Filed: Jul. 25, 2016

(86) PCT No.: PCT/JP2016/071741
§ 371 (c)(1),
(2) Date: Aug. 28, 2017

(87) PCT Pub. No.: WO2017/018383
PCT Pub. Date: Feb. 2, 2017

(65) Prior Publication Data
US 2018/0052128 A1  Feb. 22, 2018

(30) Foreign Application Priority Data
Jul. 28, 2015  (JP) ................................. 2015-148711

(51) Int. Cl.
G01R 27/02 (2006.01)
G01N 27/04 (2006.01)
(Continued)

(52) U.S. Cl.
CPC ......... *G01N 27/04* (2013.01); *G01N 15/0606* (2013.01); *G01N 15/0656* (2013.01); *G01N 1/2247* (2013.01); *G01N 2015/0046* (2013.01)

(58) Field of Classification Search
CPC ........ G01R 27/02; G01R 27/14; G01R 27/08; G01R 3/00
(Continued)

(56) References Cited

U.S. PATENT DOCUMENTS 3,839,660 A * 10/1974 Stryker ............... H01L 23/3121
174/529
4,307,061 A   12/1981 Sarholz
(Continued)

FOREIGN PATENT DOCUMENTS

JP  55-030690 A  3/1980
JP  59-197847 A  11/1984
(Continued)

OTHER PUBLICATIONS

International Search Report, PCT/JP2016/071741, dated Oct. 18, 2016, 2 pgs.

Primary Examiner — Jermele M Hollington
Assistant Examiner — Taqi R Nasir
(74) Attorney, Agent, or Firm — Volpe and Koenig, P.C.

(57) ABSTRACT

A sensor substrate according to the present invention includes an insulating substrate, a detection electrode on a principal surface of the insulating substrate, and resistance wiring including a heating electrode in the insulating substrate. The resistance wiring includes a multilayer wiring portion which is connected to the heating electrode and in which wires and other wires are connected in parallel.

14 Claims, 5 Drawing Sheets

(51) Int. Cl.
    *G01N 15/06*     (2006.01)
    *G01N 15/00*     (2006.01)
    *G01N 1/22*     (2006.01)

(58) Field of Classification Search
    USPC .......................................................... 324/691
    See application file for complete search history.

(56) References Cited

U.S. PATENT DOCUMENTS

| | | | |
|---|---|---|---|
| 4,785,243 A * | 11/1988 | Abramczyk | G01N 27/9013 324/232 |
| 5,766,780 A * | 6/1998 | Huang | B82Y 10/00 324/252 |
| 7,352,191 B2 * | 4/2008 | Mitchell | B60N 2/002 324/609 |
| 2009/0056416 A1 | 3/2009 | Nair et al. | |
| 2011/0252865 A1 | 10/2011 | Tokuda et al. | |
| 2013/0041334 A1 * | 2/2013 | Prioleau | A61F 13/42 604/361 |
| 2013/0238129 A1 * | 9/2013 | Rose | F04B 9/10 700/258 |

FOREIGN PATENT DOCUMENTS

| | | | | |
|---|---|---|---|---|
| JP | 59-225587 A | 12/1984 | | |
| JP | 11-312737 A | 11/1999 | | |
| JP | H11312737 | * 11/1999 | ............ | H01L 21/32 |
| JP | 2011-226832 A | 11/2011 | | |
| JP | 2011226832 | * 11/2011 | ............ | G01N 15/06 |

* cited by examiner

SENSOR SUBSTRATE AND SENSOR DEVICE

TECHNICAL FIELD

The present invention relates to a sensor substrate and a sensor device.

BACKGROUND ART

A sensor substrate including an insulating substrate composed of a ceramic sintered body, e.g., an aluminum-oxide-based sintered body, and a detection electrode on the surface of the insulating substrate is used as a sensor substrate applied to, for example, a sensor for exhaust gas. For example, changes in the resistance value and/or the current value due to adhesion of a detection target substance contained in the exhaust gas onto the detection electrode are detected, and the content of the detection target substance in the exhaust gas or the like is calculated and detected based on the changes in the resistance value and the current value.

In order to decompose the detection target substance adhering to the detection electrode, wiring including a heater is disposed in the insulating substrate.

CITATION LIST

Patent Literature

PTL 1: Japanese Unexamined Patent Application Publication No. 55-30690
PTL 2: Japanese Unexamined Patent Application Publication No. 59-197847

SUMMARY OF INVENTION

Technical Problem

However, the above-described sensor substrate may cause the following inconvenience. That is, in order to decompose the detection target substance adhering to the detection electrode, the heater has to generate heat well. For example, in order to decompose the detection target substance by using a heater having a high electrical resistivity, it is necessary to cause the heater to generate heat while a high voltage is applied to resistance wiring including the heater. However, there is a limitation regarding the voltage used for a sensor for exhaust gas of an internal-combustion engine or the like. Therefore, heat generation of a heater having a high electrical resistivity may be insufficient, decomposition of the detection target substance may be insufficient, and the detection accuracy may be degraded.

Solution to Problem

A sensor substrate according to an aspect of the present invention includes an insulating substrate, a detection electrode on a principal surface of the insulating substrate, and resistance wiring including a heating electrode in the insulating substrate. The resistance wiring includes a multilayer wiring portion which is connected to the heating electrode and in which wires and other wires are connected in parallel.

A sensor device according to an aspect of the present invention includes the sensor substrate having the above-described configuration and a power supply portion that supplies a potential to the heating electrode.

Advantageous Effects of Invention

A sensor substrate according to an aspect of the present invention includes an insulating substrate, a detection electrode on a principal surface of the insulating substrate, and resistance wiring in the insulating substrate and including a heating electrode. The resistance wiring includes a multilayer wiring portion which is connected to the heating electrode and in which wires and other wires are connected in parallel. Therefore, the sensor substrate includes a portion in which the electrical resistivity in the resistance wiring is reduced due to the multilayer wiring portion in the resistance wiring. As a result, the heating electrode can be made to generate heat without increasing the voltage applied to the resistance wiring, the detection target substance adhering to the detection electrode can be decomposed, and the detection accuracy can be improved.

A sensor device according to an aspect of the present invention includes the sensor substrate having the above-described configuration and, therefore, the accuracy can be improved.

DESCRIPTION OF EMBODIMENTS

Figure 1A:
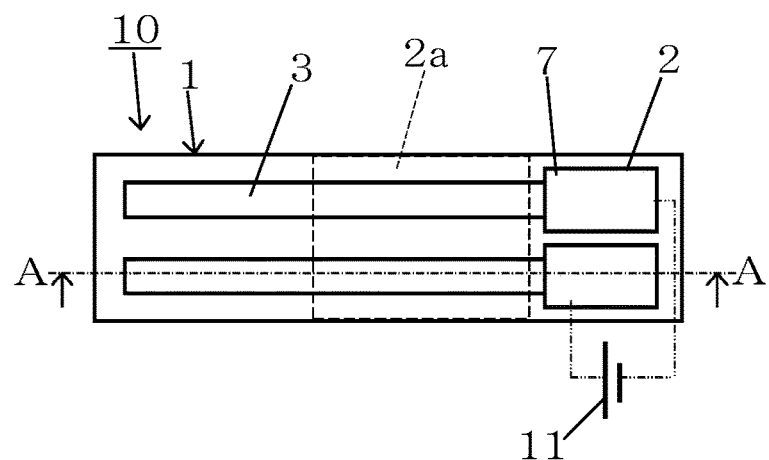
FIG. 1A is a top view illustrating a sensor substrate and a sensor device according to an embodiment of the present invention.

A sensor substrate and a sensor device according to an embodiment of the present invention will be described with reference to the attached drawings. In the following description, a distinction between top and bottom is made for the sake of convenience, and top and bottom in actual use of the sensor substrate and the like are not limited thereto.

A sensor substrate 1 includes an insulating substrate 2, a detection electrode 3 on a principal surface (upper surface in the example illustrated in FIGS. 1A and 1B) of the insulating substrate 2, and resistance wiring 5 in the insulating substrate 2 and including a heating electrode 4. The detection electrode 3 is connected to the outside by wiring conductors functioning as conductive paths.

The insulating substrate 2 is in the shape of a flat plate, for example, a rectangular plate, and is a base substrate portion to electrically insulate the detection electrode 3 from the resistance wiring 5 including the heating electrode 4. The insulating substrate 2 is formed of a ceramic sintered body, e.g., an aluminum-oxide-based sintered body, an aluminum-nitride-based sintered body, a mullite-based sintered body, a glass ceramic sintered body, or zirconia-based ceramic (zirconium-oxide-based sintered body). The insulating substrate 2 may be formed by stacking a plurality of insulating layers (not denoted by reference numerals) composed of such a ceramic sintered body.

For example, when the insulating substrate 2 is formed by stacking a plurality of insulating layers composed of an aluminum-oxide-based sintered body, the insulating substrate 2 can be formed by the following method. The insulating substrate 2 is produced by adding appropriate organic binder, solvent, and the like to a raw material powder composed of aluminum oxide, silicon oxide, magnesium oxide, calcium oxide, and the like, performing mixing to form a slurry, molding the slurry into the shape of a sheet by a doctor blade method, a calender roll method, or the like to obtain ceramic green sheets, subjecting the ceramic green sheets to appropriate punching, stacking a plurality of the resulting ceramic green sheets, as necessary, and performing firing at a high temperature (about 1,400° C. to about 1,600° C.)

The detection electrode 3 is a portion that measures the content of fine particles of soot and the like in an environment, in which the sensor substrate 1 is disposed. When fine particles of soot and the like adhere to the detection electrode 3, the electric resistance of the detection electrode 3 changes. This change in the electric resistance is detected and, thereby, the mass of fine particles in the environment, in which the detection electrode 3 is present, is calculated and detected. The content of fine particles in a gas is calculated and detected based on the mass of the fine particles and the gas flow rate (volume) in the environment in which the detection electrode 3 is present.

Therefore, the detection electrode 3 contains a metal material in which such a change in the electric resistance occurs. The metal material contains, as a primary component, a base-metal-based material catalytically inactive with respect to a fine particle decomposition reaction (hereafter simply referred to as catalytically inactive). The fine particles are, for example, soot (fine particles of carbon). The base-metal-based material that is a primary component of the metal material can form a passive film thereof on the surface (surface exposed to the outside) of the detection electrode 3. Examples of such base-metal-based materials include materials containing iron, aluminum, nickel, titanium, chromium, and silicon.

The content of the metal material in the detection electrode 3 is, for example, about 80 percent by mass or more, and the metal material is a primary component of the detection electrode 3. The detection electrode 3 may contain an inorganic component, e.g., glass or ceramic, in addition to the metal material. These inorganic components are, for example, components that adjust firing shrinkage and the like when the detection electrode 3 is formed by firing at the same time with the insulating substrate 2, as described later.

The environment, in which the sensor substrate 1 is disposed, is an exhaust passage of automobile exhaust gas, for example. If the amount of fine particles detected by the sensor substrate 1 increases, an increase in the content of fine particles that pass the exhaust passage is detected. Consequently, for example, it is possible to detect a failure of DPF (diesel particulate filter) that removes fine particles, e.g., soot, from the exhaust gas.

In order to effectively detect a change in the resistance value due to adhesion of fine particles, for example, it is preferable that the detection electrode 3 be formed to have a pattern, the length of which is easily increased, e.g., a comb-shaped pattern or a linear pattern including a slender rectangular (band-shaped) pattern. In an example illustrated FIGS. 1A and 1B, the detection electrode 3 has a slender rectangular pattern.

The wiring conductor is disposed on the upper surface of the insulating substrate 2 or in the insulating substrate 2 and is a conductive path to electrically connect, for example, the detection electrode 3 on the upper surface of the insulating substrate 2 to a connection pad 7, as described later, on the upper surface. The wiring conductor is disposed from the detection electrode 3 on the upper surface of the insulating substrate 2 to the principal surface, on which the detection electrode 3 is disposed, of the insulating substrate 2. Consequently, the detection electrode 3 electrically extends to an outer surface, e.g., the upper surface of the insulating substrate 2. In this regard, the connection pad 7 may be disposed on the lower surface of the insulating substrate 2, and the wiring conductor may be disposed from the principal surface, on which the detection electrode 3 is disposed, of the insulating substrate 2 to the other principal surface (lower surface in FIGS. 1A and 1B) on the opposite side. In this regard, the wiring conductor may include a through conductor that penetrates at least part of the insulating substrate 2 in the thickness direction. The wiring conductor may include, for example, a circuit pattern disposed between the insulating layers.

In the sensor substrate 1 according to the embodiment, the connection pad 7 for external connection is disposed on the insulating substrate 2. The connection pad 7 is directly connected to a portion that electrically extends to the upper surface of the insulating substrate 2 in the wiring conductor. Consequently, the wiring conductor is disposed from the detection electrode 3 on the upper surface of the insulating substrate 2 to the connection pad 7 on the upper surface. This wiring conductor electrically connects the detection electrode 3 to an external electrical circuit (not shown in the drawing). If the connection pad 7 is connected to a predetermined part of the external electrical circuit by using a conductive bonding material, e.g., solder or a conductive adhesive, the detection electrode 3 and the external electrical circuit are electrically connected to each other through the wiring conductor and the connection pad 7. As described later, the connection pad 7 is also disposed on the lower surface of the insulating substrate 2, and the resistance wiring 5 including the heating electrode 4 is electrically connected to the external electrical circuit through the connection pad 7. An insulating layer 2a composed of the same material as the material for forming the insulating substrate 2 may be disposed on the principal surface (upper surface) of the insulating substrate 2 such that the detection electrode 3 and the connection pad 7 are exposed.

Regarding the sensor substrate 1 according to the embodiment, the surface portion of the detection electrode 3 does not contain platinum. Therefore, the catalytic action on the chemical reaction of the detection target substance, for example, oxidation of soot, is effectively reduced compared with a detection electrode containing platinum. As a result, oxidation and the like of the detection target substance adhering to the detection electrode does not easily occur. Consequently, the sensor substrate 1 having high detection accuracy can be provided.

The surface portion of the detection electrode 3 includes a passive film. As a result, the possibility of oxidation of the entire detection electrode 3 is reduced. Therefore, the sensor substrate 1 having high detection accuracy and high long-term reliability can be provided.

As described above, the primary component of the metal material contained in the detection electrode 3 is the basemetal-based material containing at least one of iron, aluminum, nickel, titanium, chromium, and silicon, which easily forms a passive film. These base-metal-based materials are catalytically inactive and do not take a catalytic action on, for example, decomposition of fine particles. The metal material constituting the detection electrode 3 contains at least one of, for example, such base-metal-based materials in a proportion of about 80 percent by mass or more.

When the primary component of the metal material constituting the detection electrode 3 is the above-described base-metal-based material, the metal material may contain other metal components. It is not always necessary that the other metal materials easily form passive films. The other metal materials may be another type of metal material (for example, tungsten).

The detection electrode 3 is formed as described below, for example. That is, a powder of the above-described base-metal-based material is kneaded with an organic solvent and a binder to produce a metal paste, the principal surface and the like of a ceramic green sheet to be the insulating substrate 2 is coated with the resulting metal paste to form a predetermined pattern. Metal paste coating is performed by, for example, a screen printing method. Thereafter, the metal paste and the ceramic green sheet are fired at the same time. The insulating substrate 2 including the detection electrode 3 can be produced by the above-described steps.

The thickness of the passive film is set to be, for example, about 0.1 to about 5 μm. When the thickness is such an extent, the surface portion of the detection electrode 3 is effectively covered with the passive film, and the possibility of oxidation of the entirety of or most of the detection electrode 3 is effectively reduced.

It is preferable that about 90%, on an area ratio basis, of the surface portion of the detection electrode 3 include a passive film. In other words, preferably 90% or more of the exposed surface of the detection electrode 3 is covered with the passive film. Consequently, the possibility of proceeding of oxidation of the entire detection electrode 3 is effectively reduced.

It is more preferable that the entire surface portion of the detection electrode 3 include a passive film. In other words, it is more preferable that the entire region of the exposed surface of the detection electrode 3 be covered with the passive film. Consequently, the possibility of proceeding of oxidation of the entire detection electrode 3 is more effectively reduced.

If the passive film is excessively thick, the initial resistance of the surface portion of the detection electrode 3 (resistance before setting in an environment containing fine particles) increases, and it becomes difficult to detect a change in the resistance value of the detection electrode 3 due to adhesion of fine particles.

In order to form the passive film on the surface portion of the detection electrode 3, for example, the above-described firing may be performed in an atmosphere containing very small amounts of oxygen and moisture. During the firing, a passive film is generated on the exposed surface of the metal material containing the base-metal-based material. Alternatively, the detection electrode 3 may be formed of the above-described metal material and, thereafter, the sensor substrate 1 including the detection electrode 3 may be heat-treated in an environment containing very small amounts of oxygen and moisture. The exposed surface portion of the metal material is oxidized by this heat treatment, and a passive film is generated.

When the detection electrode 3 contains, for example, an iron-nickel-chromium alloy as a primary component, the passive film is an oxide layer containing at least one of iron oxide, nickel oxide, and chromium oxide. If the passive film is present on the surface portion, as described above, proceeding of oxidation up to the iron-nickel-chromium alloy present inside of the passive film of the detection electrode 3 is suppressed.

It is preferable that the metal material constituting the passive film contain an iron-nickel-chromium alloy as a primary component. That is, the base-metal-based material is preferably an iron-nickel-chromium alloy. The reason for this is as described below. The passive film containing such a base-metal-based material is formed by oxidizing a metal material containing iron, nickel, and chromium. For that purpose, the metal material contained in the detection electrode 3 is made to contain iron, nickel, and chromium. For example, these metal materials are made into a metal paste, as described above, and the detection electrode 3 is easily formed by firing the metal paste and the insulating substrate 2 (ceramic green sheet) at the same time. Also, the passive film is easily formed, and proceeding of oxidation into the detection electrode 3 is more effectively suppressed. These base metals are catalytically inactive metals that do not take a catalytic action.

Therefore, in consideration of ease of forming the passive film, that is, the measurement accuracy, the reliability, the productivity, and the like of the sensor substrate 1, the metal material constituting the detection electrode 3 is preferably an alloy material containing iron-nickel-chromium as a primary component.

The specific composition of the metal material containing an iron-nickel-chromium alloy as the base-metal-based material that is a primary component is, for example, 1 to 55 percent by mass of iron (Fe), 20 to 80 percent by mass of nickel (Ni), 10 to 25 percent by mass of chromium (Cr), 0.1 to 5 percent by mass of titanium (Ti), and 0.1 to 5 mass of aluminum (Al).

The base-metal-based material that is a primary component of the metal material for forming a passive film may contain iron and chromium. The passive film containing such a base-metal-based material is also formed by oxidation of the metal material containing iron and chromium, and the metal material included in the detection electrode 3 is made to contain iron and chromium. This metal material is made into a metal paste, and the detection electrode 3 is also easily formed by firing the metal paste and the insulating substrate 2 at the same time. The passive film is easily formed, and proceeding of oxidation into the detection electrode 3 is more effectively suppressed. These base metals are catalytically inactive metals that do not take a catalytic action.

Therefore, in consideration of ease of forming the passive film, that is, the measurement accuracy, the reliability, the productivity, and the like of the sensor substrate 1, the metal material for forming the detection electrode 3 may be an alloy material containing iron-chromium as a primary component. The iron-chromium alloy can be regarded as an alloy in which nickel has been removed from an iron-nickel-chromium alloy. The iron-chromium alloy is easily passivated compared with the iron-nickel-chromium alloy and, therefore, more easily forms a passive film on the surface portion of the detection electrode 3.

The passive film has to be disposed on the surface portion, which is exposed to an environment, e.g., outside air, of the detection electrode 3. It is not always necessary that a passive film be disposed on the surface portion, which is in contact with the insulating substrate 2, of the detection electrode 3.

When a passive film is not disposed on the surface portion, which is in contact with the wiring conductor, of the detection electrode 3, the contact resistance between the detection electrode 3 and the wiring conductor is easily reduced. Therefore, the wiring conductor can have a configuration that is advantageous for improving the electrical characteristics of the sensor substrate 1.

The passive film can be detected by cutting the sensor substrate 1 at a portion, on which the detection electrode 3 is disposed, such that a vertical cross section can be observed, and analyzing the surface portion of the detection electrode 3 by electron prove microanalysis (EPMA), X-ray diffraction analysis, or the like. In addition, the thickness of the passive film can be measured by this method.

The wiring conductor is composed of, for example, the same metal material as the detection electrode 3 and may include a passive film (not shown in the drawing) on the surface portion thereof. The wiring conductor may be composed of a hard-to-oxidize metal, e.g., platinum or gold.

The connection pad 7 can also be produced by, for example, the same method as that for the detection electrode 3 by using the same metal material as the detection electrode 3. However, if the sensor substrate 1 is used while only the detection electrode 3 and the vicinity thereof (for example, the upper surface of the insulating substrate 2) are exposed at the flow passage of the gas containing fine particles and the like, it is not always necessary that the connection pad 7 contain the above-described metal material which easily forms a passive film. That is, when the possibility of oxidation of the connection pad 7 due to a high-temperature gas or the like is low, as described above, it is not always necessary that the connection pad 7 have the oxidation resistance in contrast to the detection electrode 3.

The wiring conductor and the connection pad 7 do not detect fine particles, e.g., soot, that are the detection target substances and, therefore, may be composed of either a metal material that takes a catalytic action or other metal materials. That is, the wiring conductor and the connection pad 7 may be, for example, tungsten, manganese, cobalt, copper, gold, an alloy containing these metal materials (for example, a nickel-cobalt alloy). Regarding the wiring conductor and the connection pad 7, a material containing tungsten as a primary component may be used in consideration of, for example, ease of formation by firing at the same time with the insulating substrate 2 composed of an aluminum-oxide-based sintered body, strength of bonding to the insulating substrate 2, and characteristics, e.g., electrical resistance.

The exposed surface of the connection pad 7 may be coated with a plating layer of nickel, gold, or the like. As a result of coating with the plating layer, for example, oxidation and corrosion of the connection pad 7 can be suppressed, characteristics, e.g., wettability, of solder that connects the connection pad 7 to the external electric circuit can be improved, and the reliability and the like of the sensor substrate 1 are improved.

The detection electrode 3 may be composed of a metal material containing molybdenum silicide (for example, $MoSiO_2$) as a primary component. Here, molybdenum silicide is the above-described base-metal-based material. Alternatively, the detection electrode 3 may contain an iron-nickel-chromium alloy and molybdenum silicide as primary components.

Consequently, for example, when the above-described glass component is contained in the detection electrode 3, the glass component does not easily enter between iron-nickel-chromium particles and molybdenum silicide particles. Therefore, excessive sintering due to the glass component entering between particles does not easily occur. As a result, the oxidation resistance of the detection electrode 3 is further improved.

When the detection electrode 3 contains molybdenum silicide, the content is set to be, for example, about 90 to about 100 percent by mass. Consequently, the above-described effects can be reliably obtained.

The heating electrode 4 is included in the resistance wiring 5 and is disposed, in the insulating substrate 2, at a position corresponding to the detection electrode 3, for example, a position overlapping the detection electrode 3 in transparent plan view. Fine particles, e.g., soot, adhering to the detection electrode 3 can be decomposed by applying a voltage to the resistance wiring 5 including the heating electrode 4 and causing the heating electrode 4 to generate heat.

If the heating electrode 4 is disposed, in the resistance wiring 5, at a position nearest to the detection electrode 3, when a voltage is applied to the resistance wiring 5 including the heating electrode 4 to cause the heating electrode 4 to generate heat, heat is effectively transferred, and fine particles, e.g., soot, adhering to the detection electrode 3 can be more smoothly decomposed.

The width of the heating electrode 4 is smaller than the widths of wires 8a in a multilayer wiring portion 8 and the widths of the other wires 8b described later. It is preferable to have such a configuration because the heating electrode 4 is made to effectively generate heat by applying a voltage to the resistance wiring 5 including the heating electrode 4.

The heating electrode 4 is composed of, for example, the same metal material as the detection electrode 3. In particular, for the purpose of effective heat generation, materials containing iron, titanium, chromium, silicon, and the like having high electrical resistivities are used. The heating electrode 4 may contain a hard-to-oxidize metal, e.g., platinum or an iron-nickel-chromium alloy, as a primary component.

The content of the metal material in the heating electrode 4 is, for example, about 80 percent by mass or more, and the metal material is a primary component of the heating electrode 4. The heating electrode 4 may contain an inorganic component, e.g., glass or ceramic, in addition to the metal material. These inorganic components are components that adjust firing shrinkage when the heating electrode 4 is formed by, for example, firing at the same time with the insulating substrate 2.

When the heating electrode 4 contains an iron-nickel-chromium alloy as the metal material, in the same manner as the detection electrode 3, the composition of the metal material is, for example, 1 to 55 percent by mass of iron (Fe), 20 to 80 percent by mass of nickel (Ni), 10 to 25 percent by mass of chromium (Cr), 0.1 to 5 percent by mass of titanium (Ti), and 0.1 to 5 mass of aluminum (Al).

The heating electrode 4 is formed, for example, in the same manner as the detection electrode 3. That is, a powder of the metal material for the above-described heating electrode 4 is kneaded with an organic solvent and a binder to produce a metal paste, the principal surface and the like of a ceramic green sheet to be the insulating substrate 2 is coated with the resulting metal paste. Metal paste coating is performed by, for example, a screen printing method. Thereafter, a plurality of ceramic green sheets is stacked, as necessary, and the metal paste and the ceramic green sheets are fired at the same time. The insulating substrate 2 including the heating electrode 4 can be produced by the above-described steps.

The resistance wiring 5 is disposed in the insulating substrate 2 and includes a multilayer wiring portion 8 which is connected to the heating electrode 4 and in which wires 8a and other wires 8b are connected in parallel. When such a configuration is adopted, there is a portion, in which the electrical resistivity of the resistance wiring 5 is reduced due to the multilayer wiring portion 8 in the resistance wiring 5. As a result, when a voltage is applied to the resistance wiring 5 including the heating electrode 4, the heating electrode 4 can be made to generate heat without increasing the voltage applied to the resistance wiring 5, fine particles, e.g., soot, adhering to the detection electrode 3 can be decomposed, and the detection accuracy can be improved. In this regard, the resistance wiring 5 may be exposed at the other principal surface (lower surface) of the insulating substrate 2.

The multilayer wiring portion 8 may include through conductors that penetrate at least part of the insulating substrate 2 in the thickness direction. Therefore, the wires 8a and the other wires 8b are connected in parallel with the through conductors interposed therebetween.

In the sensor substrate 1 according to the embodiment, a connection pad 7 for external connection is disposed on the lower surface of the insulating substrate 2. The connection pad 7 is directly connected to a portion, in the multilayer wiring portion 8, that electrically extends to the lower surface of the insulating substrate 2. Consequently, the resistance wiring 5 is disposed from the inside (heating electrode 4) of the insulating substrate 2 to the connection pad 7 on the lower surface of the insulating substrate 2. The connection pad 7 is connected to a predetermined part of the external electrical circuit by using a conductive bonding material, e.g., solder or a conductive adhesive, and the heating electrode 4 and the external electrical circuit are thereby electrically connected to each other.

The multilayer wiring portion 8 is composed of, for example, the same metal material as the heating electrode 4. In particular, materials containing iron, titanium, chromium, silicon, and the like are used. The multilayer wiring portion 8 may contain a hard-to-oxidize metal, e.g., platinum or an iron-nickel-chromium alloy, as a primary component.

The content of the metal material in the multilayer wiring portion 8 is, for example, about 80 percent by mass or more, and the metal material is a primary component of the multilayer wiring portion 8. The multilayer wiring portion 8 may contain an inorganic component, e.g., glass or ceramic, in addition to the metal material. These inorganic components are components that adjust firing shrinkage when the multilayer wiring portion 8 is formed by, for example, firing at the same time with the insulating substrate 2.

When the multilayer wiring portion 8 contains an iron-nickel-chromium alloy as the metal material, in the same manner as the heating electrode 4, the composition of the metal material is, for example, 1 to 55 percent by mass of iron (Fe), to 80 percent by mass of nickel (Ni), 10 to 25 percent by mass of chromium (Cr), 0.1 to 5 percent by mass of titanium (Ti), and 0.1 to 5 mass of aluminum (Al).

The multilayer wiring portion 8 is formed, for example, in the same manner as the heating electrode 4. That is, a powder of the metal material for the above-described multilayer wiring portion 8 is kneaded with an organic solvent and a binder to produce a metal paste, the principal surface and the like of a ceramic green sheet to be the insulating substrate 2 is coated with the resulting metal paste to form a predetermined pattern of the wires 8a and the other wires 8b. Metal paste coating is performed by, for example, a screen printing method. Thereafter, a plurality of ceramic green sheets is stacked, as necessary, and the metal paste and the ceramic green sheets are fired at the same time. The insulating substrate 2 including the multilayer wiring portion 8 can be produced by the above-described steps.

In the multilayer wiring portion 8, the wires 8a and the other wires 8b are disposed in layers in the thickness direction of the insulating substrate 2 with insulating layers interposed therebetween. When such a configuration is adopted, the wires 8a and the other wires 8b connected in parallel are disposed such that the area in the plane direction of the insulating substrate 2 does not become large, and an increase in the external shape of the sensor substrate 1 can be suppressed.

Figure 2:
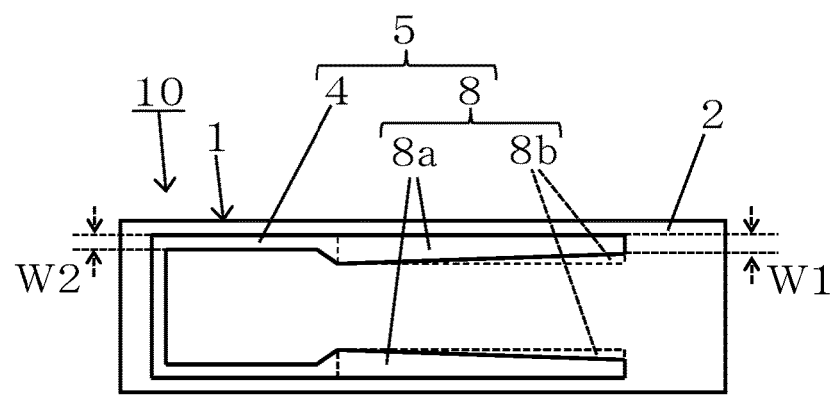
FIG. 2 is an internal top view illustrating a modified example of the sensor substrate and the sensor device illustrated in FIGS. 1A and 1B.

The widths of the wires 8a or the other wires 8b gradually decrease from end portions connected to the heating electrode 4 toward the other end portions. When such a configuration is adopted, the thermal resistance of the wires 8a or the other wires 8b can be increased, and when a voltage is applied to the resistance wiring 5 including the heating electrode 4 to cause the heating electrode 4 to generate heat, a heat loss can be suppressed. If the width W1 of the wire 8a or the other wire 8b is larger than the width W2 of the heating electrode 4, when a voltage is applied to the resistance wiring 5 including the heating electrode 4 to cause the heating electrode 4 to generate heat, a heat loss can be effectively suppressed. In the example illustrated in FIG. 2, the width of the wire 8a gradually decreases from the end portion connected to the heating electrode 4 toward the other end portion, and the width W1 of the other end portion of the wire 8a is larger than the width W2 of the heating electrode 4.

As illustrated in FIGS. 3A and 3B and FIGS. 4A and 4B, the wires 8a and the other wires 8b adjoin in the thickness direction of the insulating substrate 2 and are arranged so as not to overlap one another in transparent plan view. When such a configuration is adopted, an increase in the thickness difference in the thickness direction of the insulating substrate 2 between the region in which the multilayer wiring portion 8 including the wires 8a and the other wires 8b is disposed and the region in which the multilayer wiring portion 8 is not disposed is suppressed, deformation of the detection electrode 3, the wiring conductor, or the connection pad 7 is suppressed, and occurrence of breaking of a wire and peeling can be made difficult.

Figure 3A:
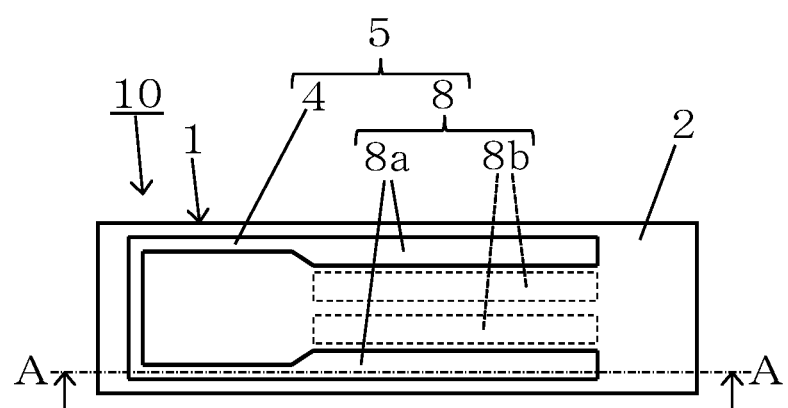
FIG. 3A is an internal top view illustrating another modified example of the sensor substrate and the sensor device illustrated in FIGS. 1A and 1B.
Figure 3B:
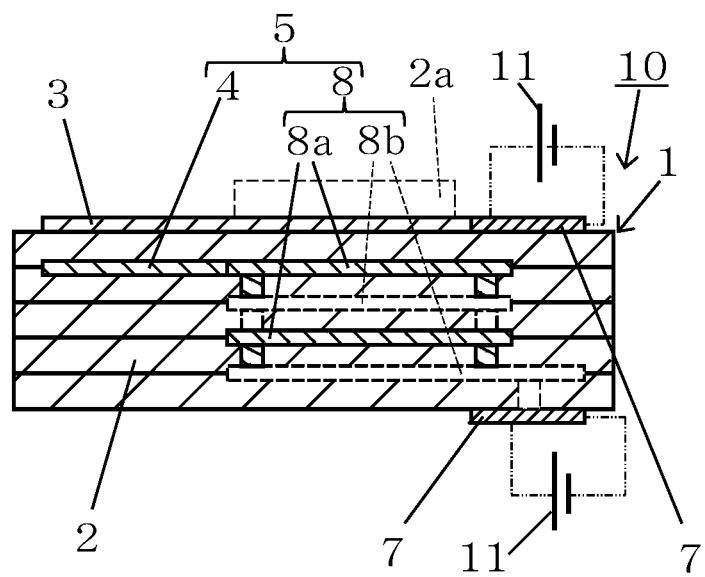
FIG. 3B is a sectional view along a line A-A shown in FIG. 3A.

As illustrated in FIGS. 3A and 3B, the other wires 8b are interposed between the wires 8a in transparent plan view. If such a configuration is adopted, when the wires 8a are connected to the heating electrode 4, the size of the heating electrode 4 can be easily made large in transparent plan view. As a result, when a voltage is applied to the resistance wiring 5 including the heating electrode 4 to cause the heating electrode 4 to generate heat, a heat generation region is increased, and fine particles, e.g., soot, adhering to the detection electrode 3 can be smoothly decomposed.

Figure 4A:
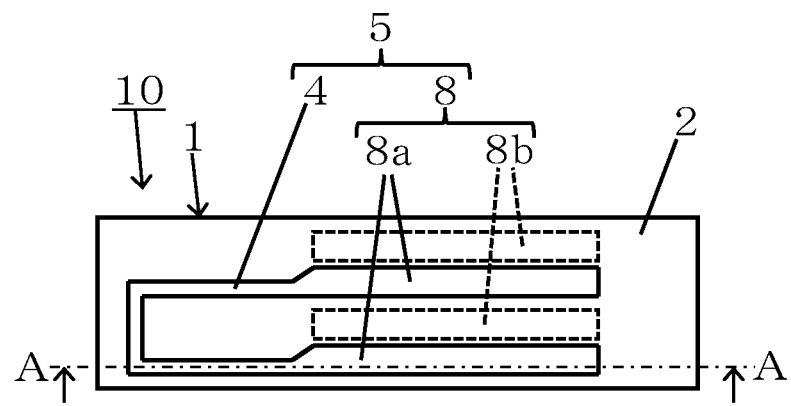
FIG. 4A is an internal top view illustrating another modified example of the sensor substrate and the sensor device illustrated in FIGS. 1A and 1B.
Figure 4B:
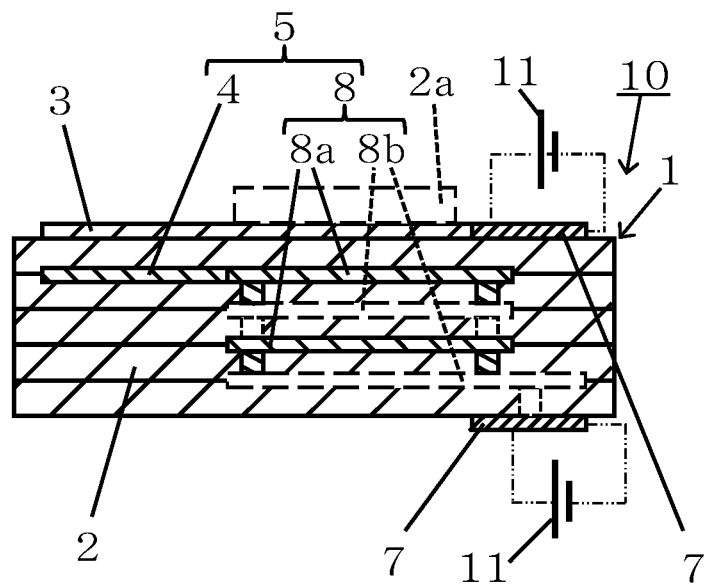
FIG. 4B is a sectional view along a line A-A shown in FIG. 4A.

As illustrated in FIGS. 4A and 4B, the wires 8a and the other wires 8b are arranged such that a portion, in which the other wire 8b is interposed between the wires 8a and the wire 8a is interposed between the other wires 8b in transparent plan view, is included. When such a configuration is adopted, the heating electrode 4 connected to the wire 8a or the other wire 8b is arranged in the region including the central portion of the insulating substrate 2 in transparent plan view, and the heating electrode 4 and, for example, a comb teeth portion, which easily has an influence on the detection characteristics of the detection electrode 3 having a comb-shaped pattern, overlap one another in transparent plan view. As a result, when a voltage is applied to the resistance wiring 5 including the heating electrode 4 to cause the heating electrode 4 to generate heat, fine particles, e.g., soot, adhering to the detection electrode 3 can be more smoothly decomposed.

A sensor device 10 according to the embodiment is formed of the above-described sensor substrate 1 and a power supply portion 11 that supplies a potential to the detection electrode 3 and the resistance wiring 5 including the heating electrode 4. Different electrodes (positive electrode, negative electrode, and the like) of the power supply portion 11 are connected to lead terminals 9 different from each other. Regarding the sensor device 10, a potential of about 50 volt (V) is supplied from the power supply portion 11 to the detection electrode 3, and a leakage current due to the potential is detected. The resistance value of the detection electrode 3 is detected by the value of the leakage current. The resistance value of the detection electrode 3 is measured by, for example, an external measurement detection circuit (not shown in the drawing). A circuit (not shown in the drawing) for measuring the resistance value of the detection electrode 3 may be arranged on the insulating substrate 2.

For example, regarding a soot detection circuit, the power supply portion 11 is composed of terminals electrically connected to an external power supply (not shown in the drawing), a rectifier, a transformation circuit, and the like and is a portion to which a predetermined electric power is transmitted from the external power supply. The transmitted electric power is adjusted, in the power supply portion 11, to conditions suitable for measurement of the resistance value of the detection electrode 3 and is transmitted to the detection electrode 3.

Figure 1B:
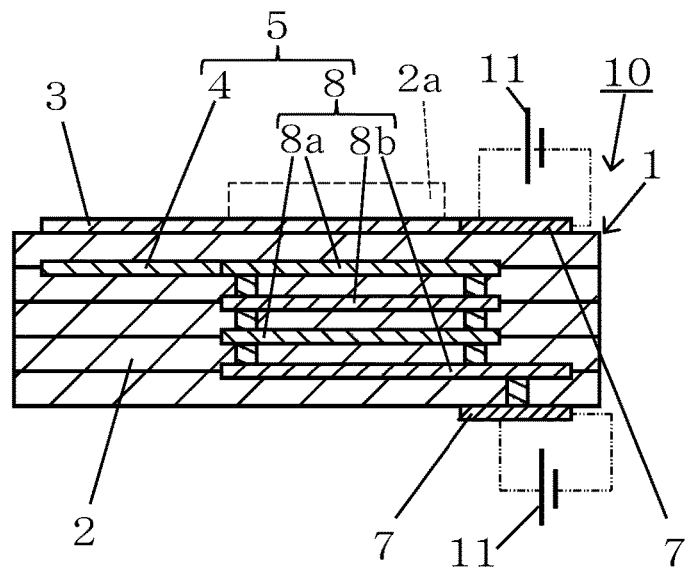
FIG. 1B is a sectional view along a line A-A shown in FIG. 1A.

Electrical connection of the power supply portion 11 to the detection electrode 3 is performed, for example, with the above-described connection pads 7 and the wiring conductors interposed therebetween. Electrical connection of the power supply portion 11 to the resistance wiring 5 including the heating electrode 4 is performed, for example, with the above-described connection pads 7 and the wiring conductors interposed therebetween. In FIGS. 1A and 1B, the connection conductors, e.g., conductive bonding materials, for electrically connecting the connection pads 7 to the power supply portion 11 are schematically indicated by imaginary lines (chain double-dashed lines).

The sensor device 10 according to the above-described embodiment includes the above-described sensor substrate 1 and, therefore, the detection accuracy is high. For example, when the detection electrode 3 is composed of platinum and the temperature of an atmosphere (exhaust gas), in which soot composed of fine particles is detected, is about 550° C., the soot is decomposed by a catalytic reaction of platinum, and the soot is not effectively detected. On the other hand, regarding the sensor substrate 1 according to the embodiment, the detection electrode 3 is catalytically inactive, decomposition of the soot is suppressed and, therefore, the content of the soot composed of fine particles is detected with high accuracy.

Figure 5A:
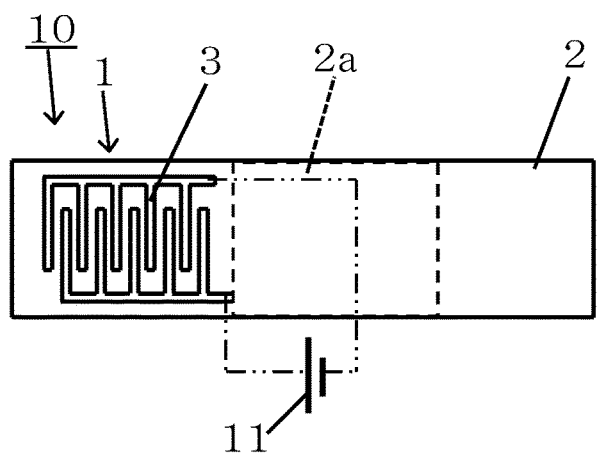
FIG. 5A is a top view illustrating another modified example of the sensor substrate and the sensor device illustrated in FIGS. 1A and 1B.
Figure 5B:
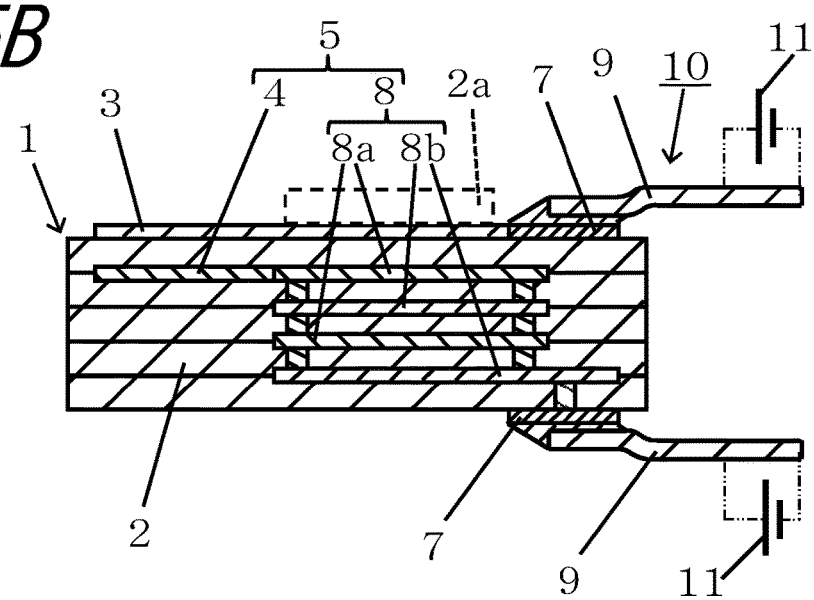
FIG. 5B is a sectional view illustrating another modified example of the sensor substrate and the sensor device illustrated in FIGS. 1A and 1B.

FIG. 5A is a top view illustrating a modified example of the sensor substrate and the sensor device illustrated in FIGS. 1A and 1B, and FIG. 5B is a sectional view illustrating another modified example of the sensor substrate and the sensor device illustrated in FIGS. 1A and 1B. In FIGS. 5A and 5B, the same portions as the portions in FIGS. 1A and 1B are indicated by the same reference numerals as those set forth above.

In the example illustrated in FIG. 5A, the detection electrode 3 has a comb-shaped pattern. In this regard, two detection electrodes 3 are disposed in an interdigital arrangement with respect to a positional relationship. Consequently, the lengths of the detection electrodes 3 can be increased while, for example, the size of the insulating substrate 2 is decreased as much as possible. As the length of the detection electrodes 3 increases, a change in the resistance value easily increases. In addition, fine particles in the gas are easily detected. That is, even if the content of fine particles in the gas is small, the fine particles can be more reliably detected.

Therefore, the sensor substrate 1 and the sensor device 10, which are more advantageous in improvement of the accuracy and sensitivity of detection of fine particles in the gas and size reduction in plan view, can be provided.

In FIG. 5A, conductors, e.g., connection pads, for electrically connecting the power supply portion 11 to the detection electrodes 3 are schematically indicated by imaginary lines (chain double-dashed lines).

In the example illustrated in FIG. 5B, a lead terminal 9 is connected to the connection pad 7. In this regard, an end portion of the lead terminal 9, the end portion being opposite to the end portion connected to the connection pad 7, is bonded and electrically connected to a predetermined portion of the external electrical circuit. That is, the sensor substrate 1 (sensor device 10) is electrically and mechanically connected to the external electrical circuit through the lead terminals 9. The different electrodes (positive electrode, negative electrode, and the like) of the power supply portion 11 are connected to lead terminals 9 different from each other. If the substrate 1 is mechanically connected to the external electrical circuit through the lead terminals 9, the stress, e.g., thermal stress, due to difference in thermal expansion between the insulating substrate 2 of the sensor substrate 1 and an external substrate (not shown in the drawing), e.g., a resin substrate, provided with the external electrical circuit is more easily relaxed by elastic deformation of the lead terminals 9. Therefore, the sensor substrate 1 and the sensor device 10, which are advantageous in improvement of, for example, the reliability of external connection, can be provided.

Each of the lead terminals 9 is not for the purpose of detecting fine particles. Therefore, the material for forming the lead terminal 9 may be appropriately selected in accordance with the use environment thereof and the conditions, e.g., productivity and economy, for the sensor substrate 1. For example, if the lead terminal 9 is composed of a metal material, e.g., platinum or gold, having good oxidation resistance, there is an advantage in the reliability of the sensor device 10. Also, economy and the like may be regarded as important, and the lead terminal 9 may be composed of an iron-based alloy, e.g., an iron-nickel-cobalt alloy, copper, or the like. When the lead terminal 9 is composed of an ion-based alloy, the exposed surface thereof may be protected by a plating layer, e.g., a gold plating layer.

The lead terminal 9 is connected to the connection pad 7 by using, for example, a brazing filler metal (not denoted by reference numeral), e.g., silver solder (silver-copper solder) or gold solder. The material for forming the brazing filler metal is appropriately selected in accordance with various conditions when the sensor substrate 1 is produced or used, in the same manner as the lead terminal 9.

The sensor substrate and the sensor device according to the present invention are not limited to the examples in the above-described embodiment and various modifications can be made within the scope of the gist of the present invention.

The invention claimed is:

1. A sensor substrate comprising:
an insulating substrate;
a detection electrode on a principal surface of the insulating substrate; and
resistance wiring in the insulating substrate and comprising a heating electrode, wherein
the resistance wiring comprises a multilayer wiring portion which is connected to the heating electrode and in which wires and other wires are connected in parallel, and
widths of the wires or the other wires gradually decrease from end portions connected to the heating electrode toward the other end portions.

2. The sensor substrate according to claim 1, wherein the wires and the other wires are disposed in layers in the multilayer wiring portion in a thickness direction of the insulating substrate.

3. The sensor substrate according to claim 1, wherein the wires and the other wires adjoin in the thickness direction of the insulating substrate and do not overlap one another in transparent plan view.

4. The sensor substrate according to claim 3, wherein the other wires are interposed between the wires in transparent plan view.

5. The sensor substrate according to claim 3, wherein the sensor substrate comprises a portion in which one of the other wires is interposed between the wires and one of the wires is interposed between the other wires in transparent plan view.

6. The sensor substrate according to claim 1, wherein the detection electrode has a comb-shaped pattern in which comb teeth portions are disposed in an interdigital arrangement.

7. A sensor device comprising:
the sensor substrate according to claim 1; and
a power supply portion that supplies a potential to the heating electrode.

8. The sensor substrate according to claim 2, wherein the wires and the other wires adjoin in the thickness direction of the insulating substrate and do not overlap one another in transparent plan view.

9. A sensor substrate comprising:
an insulating substrate;
a detection electrode on a principal surface of the insulating substrate; and
resistance wiring in the insulating substrate and comprising a heating electrode, wherein
the resistance wiring comprises a multilayer wiring portion which is connected to the heating electrode and in which wires and other wires are connected in parallel, and
the wires and the other wires adjoin in a thickness direction of the insulating substrate and do not overlap one another in transparent plan view.

10. The sensor substrate according to claim 9, wherein the wires and the other wires are disposed in layers in the multilayer wiring portion in a thickness direction of the insulating substrate.

11. The sensor substrate according to claim 9, wherein the other wires are interposed between the wires in transparent plan view.

12. The sensor substrate according to claim 9, wherein the sensor substrate comprises a portion in which one of the other wires is interposed between the wires and one of the wires is interposed between the other wires in transparent plan view.

13. The sensor substrate according to claim 9, wherein the detection electrode has a comb-shaped pattern in which comb teeth portions are disposed in an interdigital arrangement.

14. A sensor device comprising:
the sensor substrate according to claim 9; and
a power supply portion that supplies a potential to the heating electrode.

* * * * *